(12) United States Patent
Sunkara et al.

(10) Patent No.: US 7,074,969 B2
(45) Date of Patent: Jul. 11, 2006

(54) PROCESS FOR PREPARATION OF POLYTRIMETHYLENE ETHER GLYCOLS

(75) Inventors: Hari Babu Sunkara, Hockessin, DE (US); Paraskevi Parmpi, Philadelphia, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 88 days.

(21) Appl. No.: 10/871,622

(22) Filed: Jun. 18, 2004

(65) Prior Publication Data

US 2005/0283028 A1 Dec. 22, 2005

(51) Int. Cl.
C07C 41/34 (2006.01)
(52) U.S. Cl. .................. 568/621; 568/618; 568/619
(58) Field of Classification Search ............... 568/618, 568/619, 621
See application file for complete search history.

(56) References Cited

U.S. PATENT DOCUMENTS

| | | | |
|---|---|---|---|
| 2,520,733 A | 8/1950 | Morris et al. | |
| 3,326,985 A | 6/1967 | Mason | |
| 5,015,789 A | 5/1991 | Arntz et al. | |
| 5,276,201 A | 1/1994 | Arntz et al. | |
| 5,284,979 A | 2/1994 | Arntz et al. | |
| 5,334,778 A | 8/1994 | Arntz et al. | |
| 5,364,984 A | 11/1994 | Arntz et al. | |
| 5,364,987 A | 11/1994 | Arntz et al. | |
| 5,527,973 A | 6/1996 | Kelsey | |
| 5,633,362 A | 5/1997 | Nagarajan et al. | |
| 5,686,276 A | 11/1997 | Burch et al. | |
| 5,821,092 A | 10/1998 | Nagarajan et al. | |
| 5,962,745 A | 10/1999 | Arntz et al. | |
| 6,140,543 A | 10/2000 | Arntz et al. | |
| 6,232,511 B1 | 5/2001 | Arntz et al. | |
| 6,235,948 B1 | 5/2001 | Sunkara et al. | |
| 6,277,289 B1 | 8/2001 | Kurian et al. | |
| 6,284,930 B1 | 9/2001 | Deusser et al. | |
| 6,297,408 B1 | 10/2001 | Haas et al. | |
| 6,331,264 B1 | 12/2001 | Chang et al. | |
| 6,342,646 B1 | 1/2002 | Haas et al. | |
| 6,562,457 B1 | 5/2003 | Goldfinger et al. | |
| 6,590,065 B1 | 7/2003 | Goldfinger | |
| 6,599,625 B1 | 7/2003 | Goldfinger et al. | |
| 6,608,168 B1 | 8/2003 | Ng | |
| 6,720,459 B1 | 4/2004 | Sunkara et al. | |
| 6,875,514 B1 | 4/2005 | Sormani et al. | |
| 2002/0007043 A1* | 1/2002 | Sunkara et al. ............. 528/396 |
| 2002/0049356 A1 | 4/2002 | Gunatillake et al. | |
| 2004/0030060 A1 | 2/2004 | Sunkara et al. | |
| 2004/0030095 A1 | 2/2004 | Sunkara et al. | |
| 2004/0225161 A1 | 11/2004 | Sunkara et al. | |
| 2004/0225162 A1 | 11/2004 | Sunkara et al. | |
| 2004/0225163 A1 | 11/2004 | Sunkara et al. | |
| 2004/0249061 A1 | 12/2004 | Sunkara et al. | |
| 2005/0020805 A1 | 1/2005 | Sunkara et al. | |

FOREIGN PATENT DOCUMENTS

JP 2004-182974 A 7/2004
WO WO 2004/048440 A1 6/2004

OTHER PUBLICATIONS

Advanced Minerals Coporation, Comparing Conventional Diatomite and Celpure® Filter Aids, Technical Note AMC02, Version 3.5, 2002, pp. 1-2.*
Advanced Minerals Coporation, AW Celite NF Media is a High Purity, Direct Replacement for Conventiona (Food Grade) Celite Diatomite Filter Aids, http://www.advancedminerals.com/aw_celite.htm, 2003, pp. 1-3.*
U.S. Appl. No. 10/423,363, filed Apr.25, 2003.
International Search Report dated Nov. 29, 2005.
Advance Minerals Corporation, "Comparing Conventional Diatomite and Celpure Filter Aids", Technical Note AMC02, Ver. 3.5, 2002, pp. 1-2.
Advanced Minerals Corporation, "AW Celite NF Media is a High Purity, Direct Replacement for Conventional (Food Grade) Celite Diatomite Filter Aids", website: http://www.advancedminerals.com/aw_celite.htm, 2003, pp. 1-3.

* cited by examiner

*Primary Examiner*—Rosalynd Keys
(74) *Attorney, Agent, or Firm*—Mark D. Kuller; Bart E. Lerman

(57) ABSTRACT

There is disclosed a process for preparing polytrimethylene ether glycol by acid catalyzed polycondensation, neutralization and contact with filter aid. The process avoids hydrolysis and yet provides product substantially free of catalyst derived end groups.

25 Claims, No Drawings

PROCESS FOR PREPARATION OF POLYTRIMETHYLENE ETHER GLYCOLS

FIELD OF THE INVENTION

The present invention relates to a process for preparing polytrimethylene ether glycol from 1,3-propanediol or its dimers or trimers.

BACKGROUND OF THE INVENTION

Polytrimethylene ether glycol and its uses have been described in the art. It can be prepared by dehydration of 1,3-propanediol or by ring opening polymerization of oxetane.

U.S. Pat. No. 2,520,733, which is incorporated herein by reference, discloses polymers and copolymers of trimethylene glycol and a process for the preparation of these polymers from 1,3-propanediol in the presence of a dehydration catalyst such as iodine, inorganic acids (e.g. sulfuric acid) and organic acids. Polymers of molecular weight from about 100 to about 10,000 are mentioned.

U.S. Pat. No. 3,326,985, which is incorporated herein by reference, discloses a process for forming a polytrimethylene ether glycol having an average molecular weight of 1,200–1,400. First, polytrimethylene ether glycol which has an average molecular weight of about 900 is formed using hydriodic acid. This is followed by an after treatment which comprises vacuum stripping the polyglycol at a temperature in the range of 220–240° C. and at a pressure of 1–8 mm Hg in a current of nitrogen for from 1–6 hours. The polymer resulting from this process contains residues from the catalyst used.

U.S. Pat. No. 6,720,459, which is incorporated herein by reference, discloses a continuous process for preparation of polytrimethylene ether glycol from 1,3-propanediol using a polycondensation catalyst, preferably an acid catalyst.

U.S. patent application Publication No. 2002/0007043, which is incorporated herein by reference, describes a purification procedure for crude polytrimethylene ether glycol obtained from an acid catalyzed polymerization process comprising (1) a hydrolysis step to hydrolyze the acid esters formed during the acid catalyzed polymerization, (2) phase separation and water extraction steps to remove the soluble acid catalyst, generating an organic phase and a waste aqueous phase, (3) a base treatment of the organic phase to neutralize and precipitate the residual acid present, and (4) drying and filtration of the polymer to remove residual water and solids.

A method of purification of polyethers prepared using sulfuric acid catalysis is also disclosed in U.S. Patent Application Publication No. 2002/0049356, which is incorporated herein by reference. The process comprises heating the polyether with water for a period of 2 to 20 hours and at a temperature of 60 to 100° C. to substantially hydrolyze acid esters formed during polymerization, and then separating the polyether from the water. It may further include the step of washing polyether after hydrolysis with one or more additional water washes.

U.S. patent application Ser. No. 10/634,687, filed Aug. 5, 2003, (now US 2004-0225162 A1), which is incorporated herein by reference, discloses a process for improving the color of polytrimethylene ether glycol comprising contacting polytrimethylene ether glycol having color with adsorbent and separating the polytrimethylene ether glycol and adsorbent, wherein the polytrimethylene ether glycol, after contact with the adsorbent, has a molecular weight of about 250 to about 5000 and a APHA color of less than about 50.

It is clear from the prior art that when sulfuric acid is used as a catalyst to make polyether glycols from their corresponding diols, it is preferred to include a hydrolysis step because a substantial portion of the acid is converted to the ester, alkyl hydrogen sulfate. These ester groups act as emulsifying agents during the water washing process and thus cause the washing process to be difficult and time consuming and also make the acid removal incomplete. The hydrolysis step is also important in order to obtain polymer with the high dihydroxy functionality required to use the polymer as a reactive intermediate.

The purification processes disclosed in the prior art are effective in producing polytrimethylene ether glycol with high dihydroxy functionality. Often, however, it is desirable to produce short chain or low molecular weight polytrimethylene ether glycol from the polycondensation of 1,3-propanediol. As disclosed in U.S. Pat. No. 2,520,733, the trimethylene glycol polymers having molecular weights below about 200, are generally water-soluble. Polytrimethylene ether glycol with molecular weight below about 1,000 contains significant amounts of water-soluble oligomers. In addition to the solubility of oligomers in water, other factors such as the solubility of water in the low molecular polymer and interactions between polymer and water molecules may also exist. For this reason, the hydrolysis purification processes described above are very difficult for the case of low molecular weight polymers, because it is hard to achieve a distinct aqueous and organic phase separation. Also, the water washing steps utilized in the art are a substantial disadvantage, because the water washing not only removes the acid present but also removes the any water-soluble short polyether chains. Furthermore, in order to achieve high polymer yields, it is essential to recover the soluble fraction of the polymer from the water solutions, a process which is expensive and time consuming because it requires distillation of large amounts of water and creates high capital, maintenance, and operating costs.

It would be highly desirable if low molecular weight polytrimethylene ether glycol free of catalyst derived end groups, e.g. acid ester end groups derived from sulfuric acid, and other catalyst contamination could be prepared by acid catalyzed polymerization without the hydrolysis and/or water washing steps. The present invention is directed to these and other ends.

SUMMARY OF THE INVENTION

This invention is directed to a process for making polytrimethylene ether glycol comprising: (a) polycondensing reactant comprising diol selected from the group consisting of 1,3-propanediol, 1,3-propanediol dimer, 1,3-propanediol trimer and mixtures thereof in the presence of an acid polycondensation catalyst at a temperature of at least about 150° C. to obtain a polytrimethylene ether glycol reaction mixture; (b) adding to the reaction mixture substantially water-insoluble base in an amount sufficient to neutralize the acid polycondensation catalyst and obtain a neutralized reaction mixture, (c) contacting the neutralized reaction mixture with filter aid having a permeability no greater than about 0.150 Darcy, and (d) separating the polytrimethylene ether glycol from the filter aid, to obtain polytrimethylene ether glycol. Preferably the reactant comprises 90% or more by weight of 1,3-propane diol.

In one embodiment the process further comprises the step of drying the neutralized polytrimethylene ether glycol reaction mixture prior to the separation step (d).

In another embodiment the process further comprises removing unreacted reactant by distillation at reduced pressure following the separation step (d).

Preferably the polycondensation step (a) is carried out at about 160° C. up to about 210° C., more preferably up to about 200° C.

Preferably the acid polycondensation catalyst is selected from the group consisting of Bronsted acids, Lewis acids and super acids and mixtures thereof. More preferably the catalyst is selected from the group consisting of sulfuric acid, hydriodic acid, fluorosulfonic acid, p-toluenesulfonic acid, benzenesulfonic acid, methanesulfonic acid, trifluoromethanesulfonic acid, 1,1,2,2-tetrafluoroethanesulfonic acid, and 1,1,1,2,3,3-hexafluoropropanesulfonic acid. The most preferred catalyst is sulfuric acid.

The acid polycondensation catalyst is preferably used in an amount of from about 0.1 wt. %, more preferably about 0.25 wt. % up to about 1 wt. %, more preferably about 0.75 wt. %, based on the weight of the reactant.

The substantially water insoluble base is preferably selected from the group consisting of group consisting of alkaline earth metal hydroxides, alkaline earth metal oxides and alkaline earth metal carbonates. More preferably it is selected from the group consisting of calcium hydroxide, calcium oxide, calcium carbonate, magnesium hydroxide, magnesium oxide, magnesium carbonate, barium carbonate, barium oxide and barium hydroxide. The most preferred water insoluble base is calcium hydroxide.

The filter aid for use in the invention preferably comprises solid selected from the group consisting of diatomite, perlite and cellulose. A more preferred filter aid is diatomite having a permeability of from about 0.040 Darcy to about 0.140 Darcy.

In one embodiment of the invention the contacting step (c) and the separation step (d) comprise filtering the neutralized reaction mixture through filter paper coated with filter aid.

In another embodiment of the invention the contacting step (c) comprises addition of filter aid to the neutralized reaction mixture. In this embodiment, one preferred method of carrying out separation step (d) is by filtration. Another preferred method is by centrifugation.

In a preferred embodiment of the invention the acid polycondensation catalyst is sulfuric acid and the polytrimethylene ether glycol is substantially free from acid and acid ester end groups, contains less than about 5 ppm sulfur and has a molecular weight of from about 250 to about 750.

Preferably the polytrimethylene ether contains from about 0 to about 10 milliequivalents/kg of end groups derived from the catalyst, and has a number average molecular weight of about 200 to about 5,000. In a preferred embodiment the catalyst is sulfuric acid and the polytrimethylene ether glycol product has a molecular weight of about 250 to about 750, and contains from about 0 to about 10 ppm of sulfur and from about 0 to about 10 milliequivalents/kg of acid ester end groups.

The invention is also directed to polytrimethylene ether glycol having a number average molecular weight of from about 200 to about 1,000 and containing from about 0 to about 10 milliequivalents/kg of non-hydroxylic or non-olefinic end groups.

DETAILED DESCRIPTION OF THE INVENTION

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

This invention is a process for manufacture of low molecular weight polytrimethylene ether glycol using an acid polycondensation catalyst. The starting material for the process is reactant comprising at least one of 1,3-propanediol, 1,3-propanediol, dimer and 1,3-propanediol trimer, or mixtures thereof. The 1,3-propanediol reactant employed in the process of the present invention may be obtained by any of the various chemical routes or by biochemical transformation routes. Preferred routes are described in U.S. Pat. Nos. 5,015,789, 5,276,201, 5,284,979, 5,334,778, 5,364,984, 5,364,987, 5,633,362, 5,686,276, 5,821,092, 5,962,745, 6,140,543, 6,232,511, 6,235,948, 6,277,289, 6,284,930, 6,297,408, 6,331,264 and 6,342,646, all of which are incorporated herein by reference in their entireties. Preferably the 1,3-propanediol used as the reactant or as a component of the reactant will have a purity of greater than about 99% by weight as determined by gas chromatographic analysis.

Although any of 1,3-propanediol, and dimers or trimers of 1,3-propanediol can be used as the reactant in the process of the invention, it is preferred that the reactant comprise about 90% or more by weight of 1,3-propanediol. More preferably the reactant will comprise 99% or more by weight of 1,3-propanediol.

The starting material for the present invention may also contain small amounts, preferably no more than about 20%, more preferably no more than about 10%, by weight, of the starting material, of comonomer diols in addition to the reactant 1,3-propanediol or its dimers and trimers without detracting from the efficacy of the process. Examples of preferred comonomer diols include ethylene glycol, 2-methyl-1,3-propanediol, 2,2-dimethyl-1,3-propane diol and $C_6$–$C_{12}$ diols such as 2,2-diethyl-1,3-propane diol, 2-ethyl-2-(hydroxymethyl)-1,3-propane diol, 1,6-hexanediol, 1,8-octanediol, 1,10-decanediol, 1,12-dodecanediol, 1,4-cyclohexanediol, and 1,4-cyclohexanedimethanol. A more preferred comonomer diol is ethylene glycol. Poly(trimethylene-ethylene ether) glycols prepared from 1,3-propanediol and ethylene glycol are described in U.S. Patent Application Publication No. 2004/0030095, which is incorporated herein by reference. Thermal stabilizers, antioxidants and coloring materials may be added to the polymerization mixture or final product if necessary.

Any acid catalyst suitable for acid catalyzed polycondensations of 1,3-propanediol may be used in present process. Preferred acid polycondensation catalysts are described in U.S. Published Patent Application Nos. 2002/0007043 A1 and in U.S. Pat. No. 6,720,459, both of which are incorporated herein by reference. They are preferably selected from group consisting of Lewis acids, Bronsted acids, super acids, and mixtures thereof, and they include both homogeneous and heterogeneous catalysts. More preferably the catalysts are selected from the group consisting of inorganic acids, organic sulfonic acids, heteropolyacids and metal salts. Most preferably the catalyst is a homogeneous catalyst selected from the group consisting of sulfuric acid, hydriodic acid, fluorosulfonic acid, phosphorous acid, p-toluenesulfonic acid, benzenesulfonic acid, methanesulfonic acid, phosphotungstic acid, trifluoromethanesulfonic acid, phosphomolybdic acid, 1,1,2,2-tetrafluoro-ethanesulfonic acid, and 1,1,1,2,3,3-hexafluoropropanesulfonic acid, bismuth triflate, yttrium triflate, ytterbium triflate, neodymium triflate, lanthanum triflate, scandium triflate, and zirconium triflate. The catalyst can also be a heterogeneous catalyst selected from the group consisting of zeolites, fluorinated alumina, acid-treated alumina, heteropolyacids and heteropolyacids supported on zirconia, titania alumina and/or silica. The most preferred catalyst is sulfuric acid.

The polymerization process can be batch, semi-continuous, continuous, etc. A preferred batch process is described in U.S. Patent Application Publication No. 2002/0007043, which is incorporated herein by reference. In this embodiment the polytrimethylene-ether glycol is prepared by a process comprising the steps of: (a) providing (1) reactant, and (2) acid polycondensation catalyst; and (b) polycondensing the reactants to form a polytrimethylene ether glycol. The reaction is conducted at an elevated temperature of at least about 150° C., more preferably at least about 160° C., up to about 210° C., more preferably about 200° C. When it is desired to obtain a preponderance of polytrimethylene ether glycol having molecular weight of less than about 1,000, e.g. from about 200 to about 750, the temperature in step b) is preferably from about 165° C. to about 185° C.

Preferably the polytrimethylene ether glycol is prepared at atmospheric pressure or below. When the polycondensation is performed at a temperature of less than about 220° C., the preferred pressure is less than about 5 mm Hg (66 kPa); at a temperature of about 150° C., the preferred pressure is about 100 mm Hg (13 kPa) or less.

A preferred continuous process for preparation of the polytrimethylene ether glycols of the present invention is described in U.S. Pat. No. 6,720,459, which is incorporated herein by reference. Thus, in this embodiment the polytrimethylene ether glycol is prepared by a continuous process comprising: (a) continuously providing (i) reactant, and (ii) polycondensation catalyst; and (b) continuously polycondensing the reactant to form polytrimethylene ether glycol. Preferably the polycondensing is carried out in two or more reaction stages. Preferred temperatures, pressure ranges and steps are described in U.S. Pat. No. 6,720,459.

In one preferred continuous process the polycondensation is carried out in an up-flow co-current column reactor and the reactant, and polytrimethylene ether glycol flow upward co-currently with the flow of gases and vapors, preferably where the reactor has at least 3, more preferably at least 8, and up to 30 stages, more preferably up to 15 stages. The reactant can be fed to the reactor at one or multiple locations. In another preferred embodiment, the polycondensation is carried out in a counter current vertical reactor wherein the reactant and polytrimethylene ether glycol flow in a manner counter-current to the flow of gases and vapors. Preferably this reactor has two or more stages. Preferably the reactant is fed at the top of the reactor.

The amount of acid polycondensation catalyst used in the process is significant, because high acid concentrations can lead to high concentration of catalyst derived end groups in the polymer and can generate high solid waste and low polymer yields. Unduly low acid concentrations are also undesirable, because they lead to polymerization reaction rates too slow to be practical. The amount of acid will preferably be from about 0.1 wt. %, more preferably from about 0.25 wt. % to about 1 wt. %, more preferably up to about 0.75 wt. % based on the weight of the reactants. In one preferred embodiment of the invention where the acid polycondensation catalyst is sulfuric acid, a most preferred catalyst level has been found to be about 0.5 wt. %.

The reaction time for either batch or continuous polycondensation will depend on the polymer molecular weight that is desired and the reaction temperature, with longer reaction times producing higher molecular weights. In one preferred embodiment of the invention (e.g., where the catalyst is sulfuric acid) the reaction times will preferably be from about 1, more preferably from about 2 hours, and even more preferably from about 3 hours to about 20 hours, more preferably about 10 hours, and even more preferably about 6 hours.

Regardless of the conditions of the polymerization method, a critical aspect of the current invention is the purification procedure, which allows high quality product to be obtained without the time consuming, laborious and expensive hydrolysis and water washing steps of the prior art. The term "high quality" in the context of this disclosure means that the product contains high dihydroxyl functionality with little or no catalyst residues or catalyst-derived polymer end groups. For example, in one preferred embodiment (e.g., when sulfuric acid is used as the catalyst) it is found that the polytrimethylene ether glycol product contains from about 0 to about 10, preferably about 5 milliequivalents/kg of acid ester end groups, and levels of sulfur from about 0 to about 10 ppm, preferably to about 5 ppm.

In the process of the invention, the first step in purification of the crude polytrimethylene ether glycol involves neutralization of the acid polycondensation catalyst by addition to the reaction mixture of a substantially water-insoluble base. The base may be added as a dry solid, or preferably as an aqueous slurry. Preferred insoluble bases for use in the invention are metal oxides, metal hydroxides and metal carbonates. More preferred are the oxides, hydroxides and carbonates of the alkaline earth metals, examples of which are calcium hydroxide, calcium oxide, calcium carbonate, magnesium hydroxide, magnesium oxide, magnesium carbonate, barium carbonate, barium oxide and barium hydroxide. Even more preferred substantially water-insoluble bases are calcium oxide and calcium hydroxide, and the most preferred substantially water-insoluble base is calcium hydroxide. The neutralization process can be carried out at ambient room temperature or elevated temperature. A preferred temperature range is from about 40° C. to about 70° C.

The amount of insoluble base utilized in the neutralization step is preferably at least enough to neutralize all of the acid polycondensation catalyst. More preferably a stoichiometric excess of from about 0.1 wt. % to about 10 wt. % is utilized.

Purification is completed by contacting the neutralized reaction mixture with filter aid having a permeability no greater than about 0.150 Darcy, preferably from about 0.04 to about 0.140 Darcy, more preferably to about 0.80 Darcy. Filter aids are inert, finely divided, microporous solids commonly used to facilitate product throughput in filtration of polymer solutions or liquid polymers by preventing plugging of the filter screen by solids suspended in the polymer. Examples of filter aids suitable for the present invention are diatomite, perlite and cellulose. A preferred filter aid for use in the invention is diatomite.

Diatomite is a biogenic silica obtained from diatomaceous earth (also known as kieselguhr), which is a sediment enriched in biogenic silica in the form of the siliceous frustules (i.e., shells or skeletons) of diatoms. U.S. Pat. No. 5,656,568, which is incorporated herein by reference, discloses methods to make diatomite products. Perlite is a natural glass, commonly referred to as volcanic glass. Volcanic glasses are formed by the rapid cooling of siliceous magma or lava. Several types of natural glasses are known, including, for example, perlite. Finally divided celluloses suitable for use in the invention are well known in the art and commercially available from a variety of sources.

CELPURE and CELITE are commercially available forms of diatomite. HARBORLITE and FIBRA-CEL are commercial forms of perlite and cellulose respectively. A preferred filter aid for use in the present invention is CELPURE. Various grades, for example, CELPURE-65, 100, 300, 1000 are available from Advanced Minerals Corporation. CELPURE-65 and CELPURE-100 have permeabilities of from 0.040–0.08 and 0.07–0.140 Darcy respectively.

The permeability of filter aid materials reported in units of Darcies, commonly abbreviated "Da," is readily determined (Analytica-EBC of the European Brewery Convention, 4th Ed. 1987; Zurich: Braurei-und Getranke-Rundschau; E255–E258) using a specially constructed device designed to form a filter cake on a septum from a suspension of filter aid in water, and then measuring the time required for a specified volume of water to flow through a measured thickness of filter cake of known cross-sectional area The filtration processes of the invention can be optimized by selecting an appropriate grade of filter aid that maximizes process throughput, filtrate clarity and product recovery. Among these grades, the most preferable is CELPURE-65 having a permeability in the range of 0.040 to 0.080 Darcy and a surface area in the range of 6–7 $m^2/g$.

In one preferred method of carrying out the step of contacting with filter aid, the filter aid is added to the neutralized reaction mixture, preferably with enough agitation to ensure mixing. The amount of filter aid utilized will preferably be from about 0.5 wt. %, more preferably about 1 wt. % up to about 3 wt. %, more preferably about 5 wt. %, based on the weight of the product. Separation of the filter aid from the product polytrimethylene ether glycol can be achieved by centrifugation or filtration methods well known in the art. For example, filtration under the earth's gravity, centrifugal filtration, or pressure filtration can be used. Filter presses, candle filters, pressure leaf filters or conventional filter papers are also be used for the filtration, which can be carried out batchwise or continuously. A preferable filter paper is WHATMAN No 1 grade. Additional filter aid material can be used during the filtration process. The spent filter cake can be disposed as a solid waste or it can be post processed to recover product.

In another preferred method of carrying out the step of contacting with filter aid, the contacting with and separation of filter aid are carried out essentially simultaneously by filtering the neutralized reaction mixture through a bed of filter aid, which can be contained in or supported on any of the common art recognized filter apparatus, e.g., filter presses, candle filters, pressure leaf filters or conventional filter papers. In one method of carrying out the filtration, a slurry of the most appropriate grade of filter aid in a product compatible liquid is applied by methods well known in the art to a filter paper, preferably WHATMAN No 1 grade, as a thin layer of filter media precoat. When the filter aid is coated on filter paper or any other filter surface, the coating level employed is preferably at least about 0.5 kg/sq. meter, more preferably at least about 0.75 kg/sq. meter, up to about 3 kg/sq. meter, more preferably about 2 kg/sq. meter.

In one embodiment of the purification method water may be removed from the product after the addition of insoluble base but before filtration. Any conventional drying method can be used, e.g. absorption by drying agents or molecular sieves, or stripping of moisture by distillation. A particularly preferred method is stripping the moisture at reduced pressure at temperatures up to about 100° C. Following filtration of the neutralized reaction mixture, unreacted reactant, e.g. 1,3-propanediol, can be partially or completely removed by vacuum stripping at elevated temperature.

The purification process of the present invention not only removed the inorganic salts and excess insoluble base present in the polymer, but surprisingly removed the catalyst derived polymer end groups even in the absence of a hydrolysis step. In the context of this disclosure "catalyst derived polymer end groups" refers to end groups that are formed directly from the catalyst or from decomposition products of the catalyst. For example, in the case where the catalyst is hydriodic acid, the end groups found in prior art processes are iodide; in the case of sulfuric acid catalyst, the end groups found in prior art process are sulfate acid esters. The products of the present invention preferably contain from about 0 to about 10, more preferably from about 0 to about 5 milliequivalents/kg of end groups derived from the catalyst used in their preparation. Thus the end groups are almost exclusively hydroxyl and small amounts of olefinic unsaturation. That is, the polymers of the invention preferably contain from about 0 to about 10, more preferably from about 0 to about 5 milliequivalents/kg of non-hydroxylic or non-olefinic end groups Thus the process of this invention provides a high purity polytrimethylene ether glycol having a number average molecular weight preferably greater than about 200, 250, 1,000, 1,500, 1,650 or 2,000 and less than about 5,000, 4,000, 3,000, 1,000 or 750. The most outstanding benefits of the invention are manifest when the process is operated to obtain low molecular weight polytrimethylene ether glycol, i.e. having a number average molecular weight from about 200 to about 1,000 that contains significant water-soluble or water sensitive oligomer fraction. This is because for polytrimethylene ether glycol in this molecular weight range the prior art purification requiring hydrolysis and water washing steps is difficult to accomplish because of the presence of water sensitive oligomers. This not only causes the hydrolysis step to be difficult and time consuming but also can lead to yield loss.

The products produced by the process of the invention typically have a color of less than about 50 APHA, and end group unsaturation less than about 15 meq/kg. The color of the products can be further improved, if desired, by the method described in U.S. patent application Ser. No. 10/634, 687, filed Aug. 5, 2003 (now US 2004-0225162 A1), which is incorporated herein by reference.

In a preferred embodiment where the acid polycondensation catalyst is sulfuric acid, polytrimethylene ether glycol obtained by the above described process is found to have very low levels of acid ester end groups, preferably from about 0 to about 10, more preferably to about 5 milliequivalents/kg of acid ester end groups, and levels of sulfur preferably from about 0 to about 10 ppm, more preferably to about 5 ppm.

The invention is illustrated in the following examples. All parts, percentages, etc., referred to in this application (including the examples) are by weight unless otherwise indicated.

EXAMPLES

The 1,3-propanediol utilized in the examples was prepared by biological methods and had a purity of >99.8%.

The number-average molecular weights (Mn) were determined by end-group analysis using NMR spectroscopic methods.

Polydispersity (Mw/Mn) of the polymer was measured by GPC.

The acid ester end groups present in the crude polymer were identified and quantified using a proton NMR spectroscopic method. Samples were prepared for NMR analysis as follows: A Wilmad/labglass tube was filled to approximately half of its volume with chloroform-d and then 2–3 drops of crude polymer was added into the tube followed by about 0.5 ml trifluoroacetic anhydride. The tube was closed with a lid and the mixture well shaken before the NMR data were obtained.

The amount of total sulfur (from sulfuric acid and acid esters) in the polymer was determined by analyzing the samples using a wavelength dispersive X-ray fluorescence (WDXRF) spectroscopy (PANalytical Model PW2400 WDXRF spectrometer).

Color was measured as APHA values (Platinum-Cobalt System) according to ASTM D-1209.

Unsaturation was determined by ASTM D-4671.

Example 1

This example illustrates preparation of crude polytrimethylene ether glycol by the process of the invention.

To a 5 L four-neck round bottom flask were charged 3040 g (40 moles) of 1,3-propanediol (PDO) and 15.22 g (0.155 moles, 0.5% of the PDO weight) of sulfuric acid. The reaction mixture was degassed for 10 minutes under nitrogen and then heated at 170° C. for 3 hours, followed by heating at 180° C. for 4.5 hours while being stirred at 150 rpm under a nitrogen flow rate of 0.08 L/min. The reaction by-product, which is largely water, was collected continuously during polymerization. The reaction was stopped after 673 mL of water had been collected. The product polymer was analyzed for acid ester end groups and total sulfur content using NMR and XRF spectroscopic methods respectively. The acid ester chain ends in the polymer were found to be 53.9 meq/kg, and the total sulfur content in the polymer mixture was 1795 ppm.

Example 2

This example illustrates purification of the product of Example 1 by the process of the invention.

Crude polymer prepared in Example 1 was neutralized with an aqueous slurry containing 11.5 g of calcium hydroxide and 23.7 g of deionized water at 70° C. for 2 hours. The neutralized reaction mixture was dried at 100° C. for about 3 hours under reduced pressure to remove water. The dried polymer was filtered using a 4 L glass filtration unit equipped with a steam circulating outer layer. A No. 1 WHATMAN filter paper with 15 cm diameter was placed in the filtration unit and 32.2 g of CELPURE-65 (permeability in the range of 0.040 to 0.080 Darcy and surface area in the range of 6–7 $m^2/g$) was spread uniformly onto the filter paper. At the end of the filtration 2.1 kg of polymer was collected.

The NMR spectrum of the polymer showed no peak at 4.73 ppm corresponding to the acid ester groups, indicating successful separation of polymer molecules containing ester ends from the polymer containing hydroxyl and allyl ends. The total sulfur content determined by an XRF method was 2 ppm, also confirming that the polymer is essentially free of acid ester end groups and sulfuric acid.

Volatiles such as unreacted 1,3-propanediol were separated by passing the entire polymer mixture (2.04 kg) through a short path distillation apparatus under 400 mTorr pressure at 120° C. The low boiling fraction collected was 118 g. The resulting purified polymer had a number average molecular weight of 544 with a polydispersity of 1.426, and a color of 21 APHA. The unsaturation in the polymer was 13 meq/kg.

Examples 3 and 4

Experiments described in Example 1 and 2 were repeated two times under similar process conditions. The properties of the resulting crude and purified polymers are given in Table 1. The data confirm the high consistency of the process of the invention.

TABLE 1

Properties of the crude and purified polytrimethylene ether glycol

| Property | Example 3 | Example 4 |
|---|---|---|
| Acid ester ends in crude polymer, meq/kg | 58.8 | 57.9 |
| Total sulfur content in crude polymer, ppm | 1786 | 1779 |
| Acid ester ends in purified polymer, meq/kg | not detected | not detected |
| Total sulfur content in purified polymer, ppm | 3 | 3 |
| Number average molecular weight, Mn | 556 | 540 |
| Color, APHA | 16 | 13 |
| Unsaturation ends, meq/kg | 14 | 13 |

Example 5

This example, a comparative example, illustrates the poor performance of filter aid CELPURE-300, which has a permeability of 0.150–0.30 Darcy and a surface area of 3–4 $m^2/g$, outside the permeability range of no greater than about 0.150 Darcy.

Crude polymer was prepared by the procedure described in Example 1. The polymer, after neutralization with calcium hydroxide, was filtered using a filter apparatus with a Micro-media filter pad, grade M-40. CELPURE-300 was used in place of CELPURE-65 to coat the filter pad. Initially the polymer went through the filtration medium, but after a while filtration ceased as a result of plugging.

Analysis of the filtered polymer indicated a total sulfur content of 1760 ppm, demonstrating the relative ineffectiveness of CELPURE-300 in the filtration method used.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the disclosure.

What we claim is:

1. A process of making polytrimethylene ether glycol comprising:

(a) polycondensing reactant comprising diol selected from the group consisting of 1,3-propanediol, 1,3-propanediol dimer and 1,3-propanediol trimer or mixtures thereof in the presence of an acid polycondensation catalyst at a temperature of at least about 150° C. to obtain a polytrimethylene ether glycol reaction mixture; and (b) purifying the reaction mixture, without hydrolysis of the reaction mixture, to obtain polytrimethylene ether glycol by:

(i) adding to the reaction mixture substantially water-insoluble base in an amount sufficient to neutralize the acid polycondensatian catalyst and obtain a neutralized polytrimethylene ether glycol reaction mixture;

(ii) contacting the neutralized reaction mixture with filter aid having a permeability no greater than about 0.150 Darcy; and (iii) separating the polytrimethylene ether glycol from the filter aid.

2. The process of claim 1 wherein the reactant comprises 90% or more by weight of 1,3-propanediol.

3. The process of claim 1 further comprising the step of drying the neutralized polytrimethylene ether glycol reaction mixture prior to the separation step (d).

4. The process of claim 1 further comprising the step of removing unreacted reactant by distillation at reduced pressure following the separation step (d).

5. The process of claim 1 wherein the polycondensation step (a) is carried out at a temperature of from about 150° C. to about 200° C.

6. The process of claim 1 wherein the acid polycondensation catalyst is selected from the group consisting of Bronsted acids, Lewis acids and super acids.

7. The process of claim 1 wherein the acid polycondensation catalyst is selected from the group consisting of sulfuric acid, hydriodic acid, fluorosulfonic acid, p-toluenesulfonic acid, benzenesulfonic acid, methanesulfonic acid, trifluoromethanesulfonic acid, 1,1,2,2-tetrafluoroethanesulfonic acid, and 1,1,1,2,3,3-hexafluoropropanesulfonic acid.

8. The process of claim 1 wherein the polycondensation catalyst is used in an amount of from about 0.1 wt. % to about 1 wt. % based on the weight of the reactant.

9. The process of claim 8 wherein the polycondensation catalyst is used in an amount of from about 0.25 wt. % to about 0.75 wt. % based on the weight of reactants.

10. The process of claim 7 wherein the polycondensation catalyst is sulfuric acid.

11. The process of claim 1 wherein the substantially water-insoluble base is selected from the group consisting of alkaline earth metal hydroxides, alkaline earth metal oxides and alkaline earth metal carbonates.

12. The process of claim 1 wherein the substantially water-insoluble base is selected from the group consisting of calcium hydroxide, calcium oxide, calcium carbonate, magnesium hydroxide, magnesium oxide, magnesium carbonate, barium carbonate, barium oxide and barium hydroxide.

13. The process of claim 1 wherein the insoluble base comprises calcium hydroxide.

14. The process of claim 1 wherein the filter aid is selected from the group consisting of diatomite, perlite and cellulose.

15. The process of claim 1 wherein the filter aid comprises diatomite.

16. The process of claim 1 wherein the filter aid has permeability from about 0.040 to about 0.140 Darcy.

17. The process of claim 1 wherein the contacting of step (c) and the separation of step (d) comprise filtering the neutralized reaction mixture through filter paper coated with filter aid.

18. The process of claim 1 wherein the contacting of step (c) comprises addition of filter aid to the neutralized reaction mixture.

19. The process of claim 18 wherein the separation step (d) comprises filtration.

20. The process of claim 18 wherein the separation step (d) comprises centrifugation.

21. The process of claim 1 wherein the polytrimethylene ether glycol contains from about 0 to about 10 milliequivalents/kg of end groups derived from the catalyst.

22. The process of claim 10 wherein the polytrimethylene ether glycol contains from about 0 to about 10 ppm of sulfur.

23. The process of claim 10 wherein the polytrimethylene ether glycol contains from about 0 to about 10 milliequivalents/kg of acid ester end groups.

24. The process of claim 1 wherein the polytrimethylene ether glycol has a molecular weight of from about 200 to about 5,000.

25. The process of claim 1 wherein the polytrimethylene ether glycol has a molecular weight of from about 250 to about 750.

* * * * *